(12) United States Patent
Norrby

(10) Patent No.: US 7,172,669 B2
(45) Date of Patent: Feb. 6, 2007

(54) METHOD FOR APPLYING ELASTIC MEMBERS ON A PANT-SHAPED ABSORBENT ARTICLE

(75) Inventor: Niclas Norrby, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 503 days.

(21) Appl. No.: 10/791,800

(22) Filed: Mar. 4, 2004

(65) Prior Publication Data

US 2005/0000628 A1    Jan. 6, 2005

Related U.S. Application Data

(60) Provisional application No. 60/452,533, filed on Mar. 7, 2003.

(51) Int. Cl.
*A61F 13/15* (2006.01)
*B32B 37/00* (2006.01)

(52) U.S. Cl. .................. 156/164; 156/160; 156/161; 156/229; 156/256; 156/264

(58) Field of Classification Search .............. 156/160, 156/161, 163, 164, 229, 256, 264, 265, 295
See application file for complete search history.

(56) References Cited

U.S. PATENT DOCUMENTS

| | | | | |
|---|---|---|---|---|
| 4,917,746 A | * | 4/1990 | Kons et al. .................. | 156/164 |
| 5,236,539 A | * | 8/1993 | Rogberg et al. ............. | 156/495 |
| 5,330,598 A | * | 7/1994 | Erdman et al. .............. | 156/164 |
| 5,389,173 A | * | 2/1995 | Merkatoris et al. .......... | 156/164 |
| 5,413,654 A | * | 5/1995 | Igaue et al. .................. | 156/161 |
| 5,439,459 A | * | 8/1995 | Tanji et al. ............. | 604/385.28 |
| 5,440,764 A | | 8/1995 | Matsushita | |
| 5,500,075 A | * | 3/1996 | Herrmann .................... | 156/494 |
| 5,525,175 A | * | 6/1996 | Blenke et al. ............... | 156/161 |
| 5,660,664 A | * | 8/1997 | Herrmann .................... | 156/161 |
| 5,779,689 A | * | 7/1998 | Pfeifer et al. ........... | 604/385.25 |
| 6,110,158 A | * | 8/2000 | Kielpikowski ........... | 604/385.28 |

(Continued)

FOREIGN PATENT DOCUMENTS

EP    0 439 809 A2    8/1991

(Continued)

*Primary Examiner*—Jeff H. Aftergut
(74) *Attorney, Agent, or Firm*—Buchanan Ingersoll & Rooney, PC

(57) ABSTRACT

A method for applying an elastic member on an elastic web of material includes providing an elastic web of material running in a traveling direction; applying adhesive in a predetermined adhesive pattern on the web of material; applying a continuous elastic member in an elastic pattern on the adhesive, wherein the elastic member is applied in a direction of extension which deviates from the traveling direction at least within portions of the elastic member; applying a non-elastic web of material over the elastic web of material, wherein the non-elastic web of material is brought to cover the adhesive pattern, whereby the elastic member is locked between the elastic web of material and the non-elastic web of material in the applied position on the adhesive pattern. The non-elastic web of material is given a band shape with a first non-linear edge and a second non-linear edge, wherein the shape of the non-elastic web of material is brought to generally coincide with the shape of the adhesive pattern.

23 Claims, 3 Drawing Sheets

U.S. PATENT DOCUMENTS

| | | | |
|---|---|---|---|
| 6,287,409 B1 * | 9/2001 | Stephany | 156/164 |
| 6,569,275 B1 * | 5/2003 | Popp et al. | 156/229 |
| 6,689,115 B1 * | 2/2004 | Popp et al. | 604/385.27 |
| 6,808,582 B2 * | 10/2004 | Popp et al. | 156/229 |
| 6,827,804 B2 * | 12/2004 | Otsubo et al. | 156/161 |
| 2002/0023706 A1 * | 2/2002 | Vogt et al. | 156/164 |
| 2005/0133150 A1 * | 6/2005 | VanEperen et al. | 156/164 |

FOREIGN PATENT DOCUMENTS

| | | |
|---|---|---|
| EP | 0 588 367 A1 | 3/1994 |
| EP | 0 694 297 A1 | 1/1996 |
| EP | 1 249 214 A2 | 10/2002 |
| WO | WO 97/00654 A1 | 1/1997 |

* cited by examiner

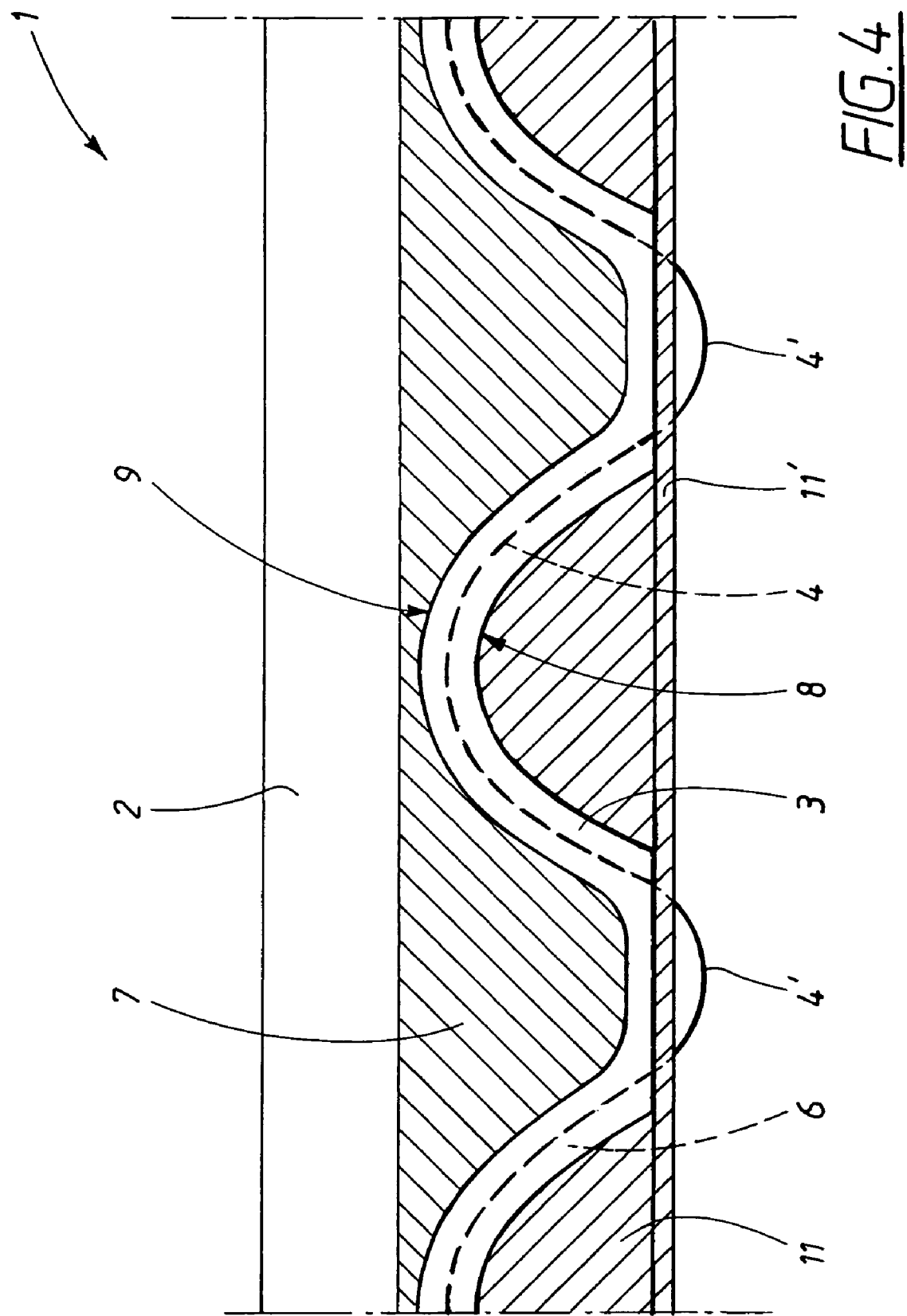

METHOD FOR APPLYING ELASTIC MEMBERS ON A PANT-SHAPED ABSORBENT ARTICLE

CROSS-REFERENCE TO RELATED APPLICATION

This application claims priority under 35 U.S.C. § 119 to U.S. Provisional Application No. 60/452,533 entitled "Method for Applying Elastic Members on a Pant-shaped Absorbent Article" and filed on Mar. 7, 2003, the entire content of which is hereby incorporated by reference.

TECHNICAL FIELD

The invention pertains to a method for applying an elastic member on an elastic web of material comprising providing an elastic web of material running in a travelling direction; applying adhesive in a predetermined adhesive pattern on the web of material; applying a continuous elastic member in an elastic pattern on the adhesive, wherein the elastic member is applied in a direction of extension which deviates from the travelling direction at least within portions of the elastic member; applying a non-elastic web of material over the elastic web of material, wherein the non-elastic web of material is brought to cover the adhesive pattern, whereby the elastic members are locked between the elastic web of material and the non-elastic web of material in the applied position on the adhesive pattern. The invention aims particularly at offering a method of manufacturing elastic pant diapers.

BACKGROUND ART

It has become increasingly more common to manufacture incontinence protectors in the form of pant diapers. Such pant diapers include an outer panty having an integral absorbent inner part. Alternatively, an outer panty can be used together with a separate incontinence shield which is temporarily attached inside the outer panty and which, thus, can be changed for a new incontinence shield while retaining the same outer panty. Both kinds of incontinence protectors are manufactured for infants as well as for incontinent adult persons.

The pants concerned here are of the disposable kind, implying that the pant diaper or diaper pant is intended to be discarded after use and not washed or otherwise restored for use. This means that the materials and production methods which are available are those which are cost efficient and which do not result in articles having an exceedingly high price. In particular, it must be possible to perform the different process operations at high speed, which puts certain limitations on the choice of method.

In order to obtain a good fit and to achieve a tight seal in pant diapers and diaper pants, these types of absorbent articles are often manufactured at least partly from elastic materials. For instance, all of the belly-encircling part or only the side panels may be made from elastic nonwoven material. In this manner, a good fit and a certain size adaptation is achieved. The elastic material in the panty itself is usually supplemented with particular elastic members which are arranged around the leg openings and the waist opening of the panty. Such elastic members give a locally higher tightening and ensure that the panties will not slide down. Moreover, the elastic members seal against leakage past the openings in the panty. However, a problem arises when the elastic members are to be attached to a material which is in itself elastic. In order to keep the elastic members in place, adhesive is usually applied to the elastic material, whereafter the elastic elements are laid down on the adhesive. Thereafter, the elastic members are locked in the applied position by laminating a further material layer over the elastic material layer and the elastic members. For cost reasons, it is generally unsuitable to use a further elastic material layer as a locking material. Instead, an ordinary non-elastic material layer is used, such as a nonwoven. This means that the elastic properties in the elastic material layer are strongly reduced and in some instances in fact completely extinguished in the laminated area, which of course is an unwanted result of the lamination.

Consequently, an objective of the present invention is to provide a method for application of elastic members on an elastic web of material, wherein the elastic elements are locked onto the elastic web of material with minimal negative impact on the elastic properties of the elastic web of material.

SUMMARY OF THE INVENTION

In accordance with the present invention there has been provided a method of the kind mentioned in the introduction, which method substantially removes the problems with previously known methods of application of elastic members on an elastic web of material.

The method in accordance with the present invention is primarily distinguished by the non-elastic web of material being given a band shape with a first non-linear edge and a second non-linear edge, wherein the shape of the non-elastic web of material is brought to generally coincide with the shape of the adhesive pattern.

The first non-linear edge of the non-elastic material web is preferably formed by cutting the material web before laying down the non-elastic material web on the elastic material web.

In accordance with a preferred embodiment of the invention, the second non-linear edge of the non-elastic material web is formed after laying down the non-elastic material web on the elastic material web.

The elastic material web may constitute a component in a production web for the production of hygienic panties, wherein leg openings are cut out in the production web. Hence, the second non-linear edge of the non-elastic material web is formed when cutting the leg openings.

The hygienic panties can be absorbent hygienic panties or pant diapers, wherein the absorbent cores are applied to the production web between the leg openings.

In accordance with a further preferred embodiment of the invention, the elastic member is laid down on the elastic material web in a sinus-curve shape.

It is also possible to arrange the elastic member so that, along parts of its length, it is laid down outside of the elastic material web. In this manner, the parts of the elastic member which are laid down outside the elastic material web can be cut away after application of the non-elastic material web.

The elastic member may be a single elastic member, such as an elastic band or an elastic thread. Alternatively, the elastic member may comprise at least two part-members.

In accordance with the a preferred embodiment of the invention, the non-elastic material web is advantageously constituted by a nonwoven material; and the elastic material web is advantageously constituted by a three-layer laminate having a nonwoven layer attached to each side of an apertured elastic film.

BRIEF DESCRIPTION OF THE DRAWINGS

In the following, the present invention will be described more closely with reference to the figures which are shown in the appended drawings.

FIG. 4 is a production web in accordance with an alternative preferred embodiment of the invention.

DETAILED DESCRIPTION OF THE PREFERRED EMBODIMENTS

Figure 1:
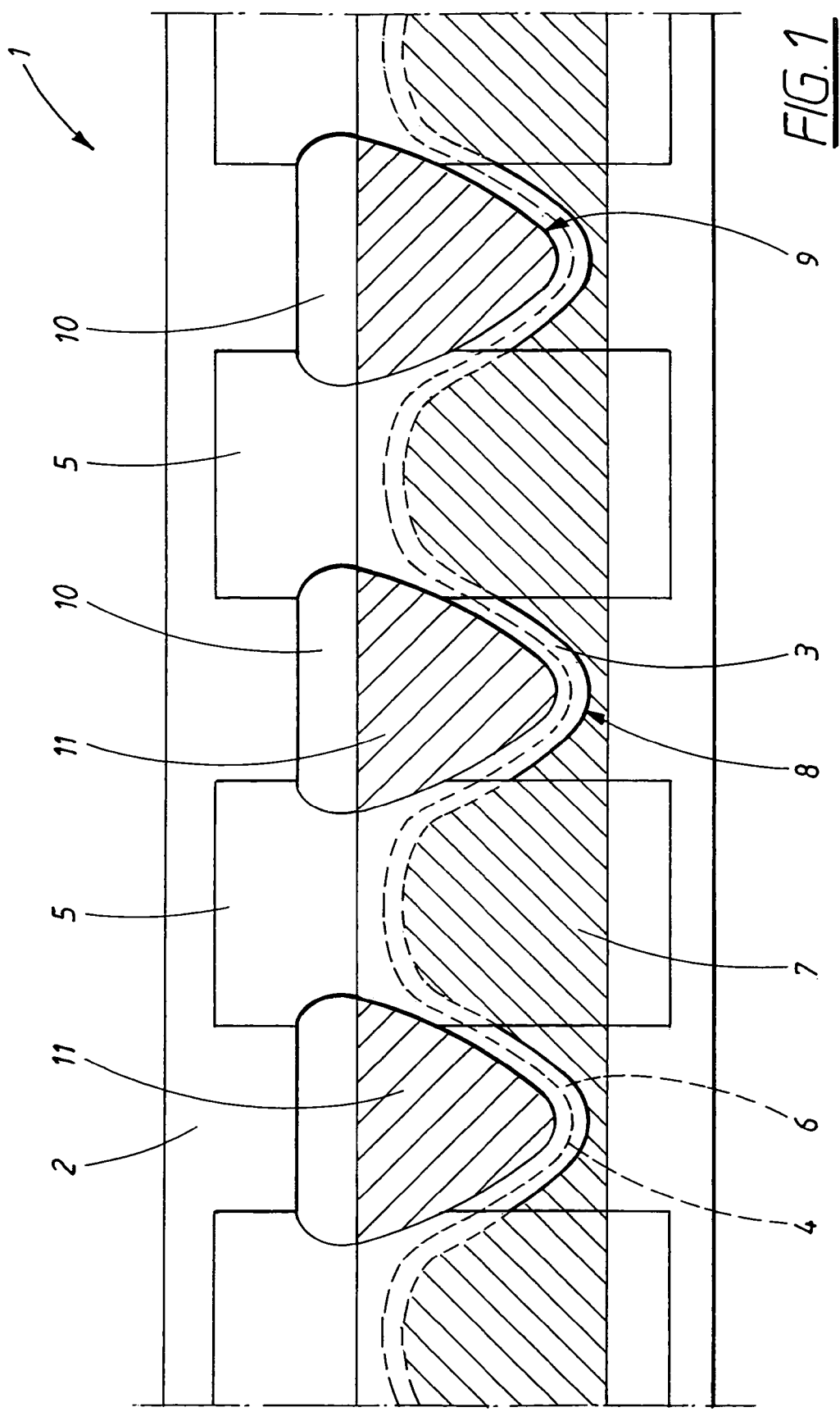
FIG. 1 is a production web in accordance with a preferred embodiment of the present invention.

The production web 1 which is shown in FIG. 1 is preferably made up of an elastic web of material 2, a non-elastic web of material 3, an elastic member 4, and a number of core packages 5, which are distributed on the elastic web of material at a predetermined mutual distance from each other. The production web is shown in FIG. 1 in a stage when all components are assembled but before the web is converted into individual articles. The shown production web 1 is intended to be converted into pant diapers in subsequent process steps.

The production web 1 is formed in a continuous process wherein the elastic web of material 2 is fed in a direction of production coinciding with the length direction of the elastic web of material. A coating of adhesive is applied in a curve shaped area 6 on the elastic web of material 2, whereafter the elastic member 4 is fixed to the adhesive. In the shown example, the adhesive is applied along a generally sinus-shaped curve. The adhesive can be applied with any method suitable for the purpose, such as spraying, or coating. The adhesive that is used is preferably a hot melt adhesive which is applied in a melted form and which solidifies upon cooling. In order to keep the elastic member in place in the curve-shaped pattern, the non-elastic web of material 3 is subsequently applied over the adhesive-coated surfaces and over the elastic element 4, whereby the elastic member is firmly locked between the two webs of material 2,3.

Before the non-elastic web of material 3 is laid down on the elastic web of material 2, an edge portion 7 is cut or trimmed away along a curve-shaped cut line 8, which generally coincides with a corresponding curve-shaped edge on the curve-shaped adhesive area. The cut line 8 is adapted so that the non-elastic web of material 3 will completely cover the curve-shaped adhesive area when the non-elastic web of material 3 is laid down on the elastic web of material 2. The portion 7, which is cut away before laying down the non-elastic web of material 3, is marked with slanting lines in FIG. 1.

After the elastic element 4 has been attached between the elastic web of material 2 and the non-elastic web of material 3, the core packages 5 are applied at a predetermined mutual distance on the elastic web of material 2.

The core package 5 can be attached to the production web 1 over the entire common surface or over only parts thereof. For instance, the core packages 5 can be attached only along a line or a band-shaped area extending centrally over each core package 5 in the length direction of the core packages which coincides with the transverse direction of the production web. Alternatively, the core packages can be attached along one or several transversely or longitudinally extending lines or band-shaped areas. It is also possible to attach the core packages 5 with a number of scattered attachment points or attachment areas. The attachment of the core packages 5 can be made with any suitable method such as welding or gluing.

After the application of the core packages 5, leg recesses 10 are cut out from the production web 1 between each core package 5 and with a shape which conforms to the shape of the elastic element 4 and the curve-shaped adhesive area 6. When the leg recesses 10 are cut out, the non-elastic web of material 3 is shaped simultaneously by removing substantially triangular portions 11 of the non-elastic web of material 3. Hereby, the remaining part of the non-elastic web of material 3 presents a band-shape which corresponds to the shape of the curve-shaped adhesive area 6. As is apparent from FIG. 1, the finally cut-out non-elastic web of material 3 has a curve-shape with a first curve-shaped cut edge 8 on one side of the elastic member 4 and a second curve-shaped edge 9 running along a part of the edge of each leg recess 10 and with a straight segment between the leg recesses 10. Accordingly, the non-elastic web of material 3 has been given a shape which is adapted to the shape of the elastic member 4 and covers only the elastic member 4 and the surrounding adhesive-coated area 6. This means that the non-elastic web of material 3 only marginally affects the elasticity of the elastic web of material 2.

After cutting out the leg recesses 10 and removing the cut-out portions, the production web 1 is folded double in the direction of production so that a folded edge and an open edge are formed. The folded production web 1 is joined together intermittently transversely to the direction of production, the joinings extending from the open edge of the production web 1 to the edge of each of the leg openings 10. The joinings are formed in a way known in the technical area for instance by welding or gluing and are suitably openable. This implies that the joining should break before the surrounding material when the joined parts are being pulled apart. However, it is naturally necessary that the joinings are sufficiently strong to keep the finished pant diaper together during use.

The folded and joined production web 1 is subsequently divided by being cut at the centre of each joining, so that individual pant diapers are separated from the production web 1. The finished absorbent pant diapers may then pass through further process steps such as folding and packing.

During manufacture of the pant diapers it is naturally also possible to apply additional components which are not described herein, such as raised leakage barriers and the like. Such components are common in absorbent articles but are not of significance to the present invention.

Figure 2:
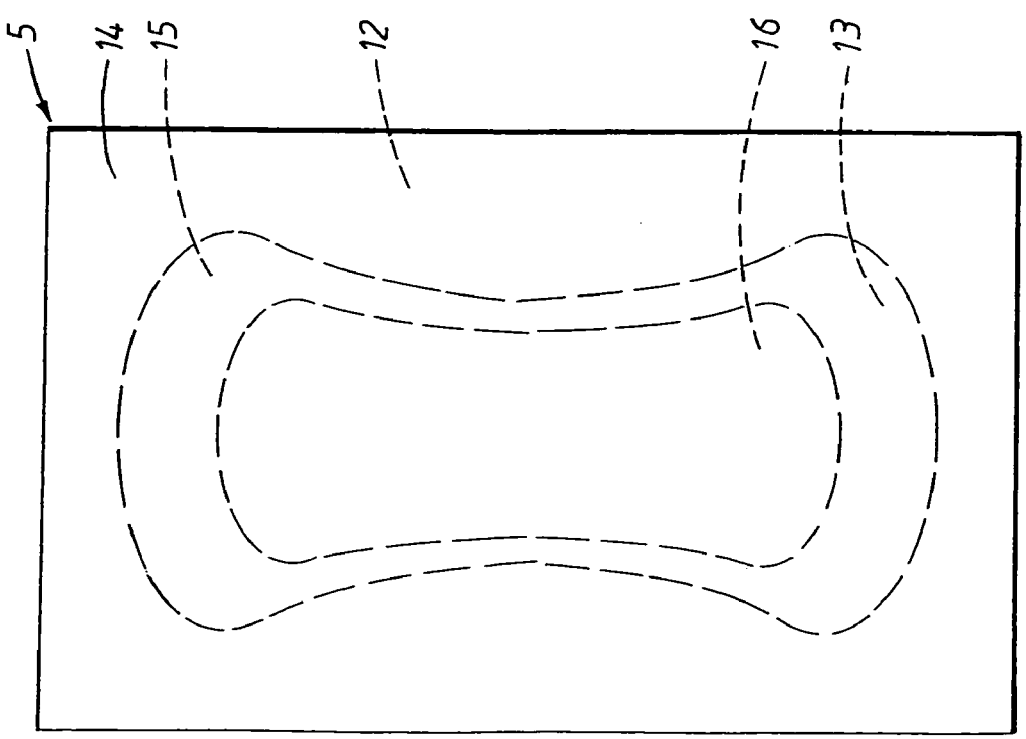
FIG. 2 is an absorbent package.

A core package 5 which is suitable for pant diapers is best shown in FIG. 2 and comprises a liquid barrier layer 12, an absorbent core 13 and a liquid permeable inner layer 14. The core package 5 is attached with the liquid barrier layer 12 against the elastic web of material 2. FIG. 2 shows an absorbent core 13 having two superposed absorbent layers 15,16, wherein the lower absorbent layer 15 which is located closest to the liquid barrier layer 12 is somewhat larger than the upper absorbent layer 16 which is located closest to the inner layer 14. In the shown example, the core package 5 has a rectangular planar shape, being defined by the shape of the liquid barrier layer 12 and the liquid permeable inner layer 14 which together enclose the absorbent core 13. When the core package 5 is placed on the production web 1, as shown in FIG. 1, parts of the liquid permeable inner layer 14 and the liquid barrier layer 12 will be trimmed away when cutting out the leg openings 10, whereby the core package 5 is given a more hourglass-like planar shape. It is naturally possible to use core packages 5 having other planar shapes, the liquid barrier layer 12 and the inner layer 14 may, for instance, already from the start be shaped after the leg openings of the diaper. It is also possible to use core packages 5 having a trapezoid shape, an oval shape, etc. Further, the core package 5 does not need to have the shape that is shown in the figure. For instance, for absorbent panties intended as protectors for light incontinence or sanitary napkins, it may be sufficient with an absorbent core 13 which is placed mainly in the crotch portion of the absorbent panty.

The liquid permeable inner layer 14 may include any material known for the purpose, such as layers of nonwoven material, perforated plastic film, netting, tow, or the like. The inner layer 14 may, of course, also include a laminate of two or more layers of the same or different material.

The liquid barrier layer 12 may include a liquid impermeable plastic film, a hydrophobic nonwoven layer or a nonwoven layer which has been treated to have liquid barrier properties, or any other flexible material layer which has the ability to resist liquid penetration. However, it may be an advantage if the liquid barrier layer 12 exhibits a certain breathability, i.e. allows passage of water vapour through the layer 12.

The absorbent core 13 can be formed from absorbent materials such as cellulose fluff pulp, tissue, absorbent foam, etc. It is also common that the absorbent core 13 comprises superabsorbents, i.e. polymeric materials which can absorb body fluids corresponding to several times their own weight while forming an aqueous gel. Such superabsorbents usually exist in the form of particles, but fibres, flakes, granules and film are also found. In addition, the absorbent core 13 may comprise non-absorbent components such as stiffening elements, shaping elements, binders, etc. Different kinds of liquid receiving and liquid distributing structures such as fibrous wadding, open-cell foam, wicking layers or similar may also be included in the core package 5.

The different components that are included in the core package 5 may be connected to each other in a conventional manner, for instance by gluing or welding by heat or ultrasonically. Evidently, the core package 5 may comprise further components apart from those which have been described here, for instance the core package may comprise liquid transport layers, elastic elements, shape stabilising elements, shaping elements, or the like. Even if the absorbent core has been shown having two absorbent layers 15, 16, alternative arrangements can be used. For some applications it may, for instance, be sufficient with a single absorbent layer while other applications may require more than two absorbent layers. Thus, the design of the absorbent core can be adapted to the amount of liquid that the absorbent core is expected to absorb. Similarly, the kind of body fluids that are to be absorbed and the manner in which the body fluids are delivered to the absorbent core are naturally of importance for the size and properties of the absorbent core.

Figure 3:
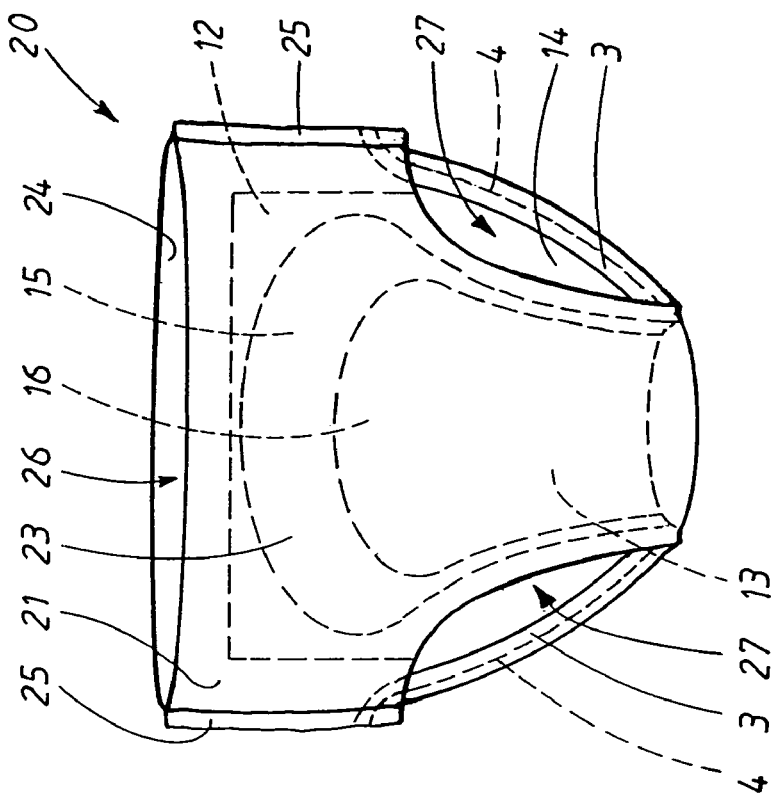
FIG. 3 is a pant diaper manufactured by a method in accordance with the present invention.

The pant diaper 20 shown in FIG. 3 comprises an elastically stretchable outer panty 21, which is formed from the elastic web of material 2. Suitable elastic materials are different kinds of elastic nonwoven materials. Further, the elastic material in the outer panty 21 may include a laminate. An elastic nonwoven material that is suitable for use in an absorbent panty in accordance with the invention should preferably be able to be elastically stretched at least 80% and preferably at least 100% in the transverse direction of the panty in order to provide sufficient elastic seal around the edges of the leg openings on the front portion of the absorbent panty. It is further advantageous if the elastic nonwoven material can be elastically stretched also in the length direction of the absorbent panty, i.e. in a direction perpendicular to the transverse direction.

In an extended planar but assembled state as shown in FIG. 3, the front portion 23 of the pant diaper 20 is joined to the corresponding rear portion of the pant diaper in two side joints 25. In this manner a waist opening 26 and two leg openings 27 are formed.

As has been previously mentioned, the side joints 25 are suitably formed in such a way so that they can resist the pulling forces which arise during putting on and wearing the pant diaper but so that they can be torn apart when removing the used absorbent panty.

Elastic members 4 are arranged as leg elastic on the rear portion 24 of the pant diaper and follow the rear edge of the leg openings 27. Thus, the elastic elements 4 around the leg openings are only arranged in the rear portion 24 of the pant diaper while the part of the leg edges 15 which extends over the front portion 23 is free from special elastic members. Since the outer panty 21 comprises elastic material it is not necessary that the waist opening 26 is provided with special elastic elements, the elasticity of the outer panty 21 for many applications being sufficient to make the pant diaper 21 sit securely and comfortably in place and to seal around the waist of the user. An alternative in order to obtain enhanced elastic effect around the waist opening 26 is to fold the elastic material in the outer panty 2 so that a lining having increased resistance to stretching is formed around the waist opening 26. Within the scope of the invention, it is naturally also possible to arrange elastic members around the waist opening. Such elastic members are applied along one or both edges of the production web 1 shown in FIG. 1.

The elastic members 4 in the leg elastic and in any waist elastic may be in the form of elastic threads, bands or similar. If elastic threads or bands are used, two or more of those are often arranged parallel to each other and will then constitute elastic part members in the elastic member. The material in the elastic member may be rubber, elastic foam, or similar.

Although the described pant diaper is only provided with elastic members along the rear parts of the leg openings, it is naturally conceivable to arrange elastic along the front parts of the leg openings either alternatively or as a complement.

In FIG. 4 is shown a production web 1, which comprises an elastic web of material 2, a non-elastic web of material 3, and an elastic member 4. The elastic member 4 is attached between the elastic web of material 2 and the non-elastic web of material 3 in an adhesive area 6. Parts 4' of the elastic member 4 run outside the edge of the production web and are cut or trimmed away along a curve-shaped cut edge 8 together with a cut-away portion of the non-elastic web of material 3 and the elastic web of material 2. The cutting is advantageously performed in two steps: a thin straight edge segment 11' being cut off in a first step and the rest of the undesired portions being cut off in a later production step, possibly after joining of the production web 1 with further production components. The opposite edge of the non-elastic web of material is also given a curve-shaped cut edge 9. This is suitably made before the non-elastic web of material 3 is joined to the elastic web of material. The removed portions 7,11 of the non-elastic web of material 3 are hatched in FIG. 4.

The production web 1 which is shown in FIG. 4 is intended to be included as a component in the manufacture of absorbent articles where it is not desired that the elastic element 4 extends unbroken over the article. In addition, it may be desirable to manufacture absorbent articles having only some parts which are elastically stretchable. For example, it is common to design pant diapers with an elastic part encircling the lower torso but having a non-elastic crotch portion. To this end, the elasticated elastic production web in FIG. 4 can be combined with further webs of material to form a complete production web.

The invention claimed is:

1. A method for applying an elastic member on an elastic web of material comprising:
    providing an elastic web of material running in a travelling direction;
    applying adhesive in a predetermined adhesive pattern on the web of material;
    applying a continuous elastic member in an elastic pattern on the adhesive, wherein the elastic member is applied in a direction of extension which deviates from the travelling direction at least within portions of the elastic member;
    applying a non-elastic web of material over the elastic web of material, wherein the non-elastic web of material is brought to cover the adhesive pattern, whereby the elastic member is locked between the elastic web of material and the non-elastic web of material in the applied position on the adhesive pattern;
    wherein the non-elastic web of material is given a band shape with a first non-linear edge and a second non-linear edge and the shape of the non-elastic web of material is brought to generally coincide with the shape of the adhesive pattern.

2. The method according to claim 1, wherein the first non-linear edge of the non-elastic material web is formed by cutting the material web before laying down the non-elastic material web on the elastic material web.

3. The method according to claim 1, wherein the second non-linear edge of the non-elastic material web is formed after laying down the non-elastic material web on the elastic material web.

4. The method according to claim 3, wherein the elastic material web constitutes a component in a production web for the production of hygienic panties, wherein leg openings are cut out in the production web, the second non-linear edge of the non-elastic material web being formed when cutting the leg openings.

5. The method according to claim 4, wherein a plurality of absorbent cores are applied to the production web between the leg openings.

6. The method according to claim 1, wherein the elastic member is laid down on the elastic material web in a sinus-curve shape.

7. The method according to claim 1, wherein the elastic member, along at least one part of its length, is laid down outside of the elastic material web.

8. The method according to claim 7, wherein the at least one part of the elastic member which is laid down outside the elastic material web is cut away after application of the non-elastic material web.

9. The method according to claim 1, wherein the elastic member comprises at least two part-members.

10. The method according to claim 1, wherein the non-elastic material web is constituted by a nonwoven material.

11. The method according to claim 1, wherein the elastic material web is constituted by a three-layer laminate having a nonwoven layer attached to each side of an apertured elastic film.

12. A method for applying an elastic member on an elastic web of material comprising:
    providing an elastic web of material running in a travelling direction;
    applying adhesive in a predetermined adhesive pattern on the web of material;
    applying a continuous elastic member and a non-elastic web of material on the adhesive such that the non-elastic web of material is brought to cover the adhesive pattern, wherein the elastic member is applied in a direction of extension which deviates from the travelling direction at least within portions of the elastic member and the elastic member is retained between the elastic web of material and the non-elastic web of material;
    wherein the non-elastic web of material is given a band shape with a first non-linear edge and a second non-linear edge and the shape of the non-elastic web of material is brought to generally coincide with the shape of the adhesive pattern.

13. The method according to claim 12, wherein the first non-linear edge of the non-elastic material web is formed by cutting the material web before laying down the non-elastic material web on the elastic material web.

14. The method according to claim 12, wherein the second non-linear edge of the non-elastic material web is formed after laying down the non-elastic material web on the elastic material web.

15. The method according to claim 13, wherein the second non-linear edge of the non-elastic material web is formed after laying down the non-elastic material web on the elastic material web.

16. The method according to claim 14, wherein the elastic material web constitutes a component in a production web for the production of hygienic panties, wherein leg openings are cut out in the production web, the second non-linear edge of the non-elastic material web being formed when cutting the leg openings.

17. The method according to claim 16, wherein a plurality of absorbent cores are applied to the production web between the leg openings.

18. The method according to claim 13, wherein the elastic member is laid down on the elastic material web in a sinus-curve shape.

19. The method according to claim 13, wherein the elastic member, along at least one part of its length, is laid down outside of the elastic material web.

20. The method according to claim 19, wherein the at least one part of the elastic member which is laid down outside the elastic material web is cut away after application of the non-elastic material web.

21. The method according to claim 13, wherein the elastic member comprises at least two part-members.

22. The method according to claim 13, wherein the non-elastic material web is constituted by a nonwoven material.

23. The method according to claim 13, wherein the elastic material web is constituted by a three-layer laminate having a nonwoven layer attached to each side of an apertured elastic film.

* * * * *